(12) United States Patent
Launay et al.

(10) Patent No.: US 10,576,417 B2
(45) Date of Patent: Mar. 3, 2020

(54) HYDROCHLORIC ACID PURIFICATION PROCESS AND PLANT

(71) Applicant: Arkema France, Colombes (FR)

(72) Inventors: Marianne Launay, Serezin du Rhone (FR); Irene Emery, Francheville (FR); David Jean-Leopold Bidet, Oullins (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/096,307

(22) PCT Filed: Apr. 11, 2017

(86) PCT No.: PCT/FR2017/050864
§ 371 (c)(1),
(2) Date: Oct. 25, 2018

(87) PCT Pub. No.: WO2017/191388
PCT Pub. Date: Nov. 9, 2017

(65) Prior Publication Data
US 2019/0134560 A1    May 9, 2019

(30) Foreign Application Priority Data

May 3, 2016   (FR) ..................... 16 54010

(51) Int. Cl.
*B01D 53/68* (2006.01)
*B01D 53/70* (2006.01)
(Continued)

(52) U.S. Cl.
CPC ........... *B01D 53/685* (2013.01); *B01D 53/68* (2013.01); *B01D 53/70* (2013.01); *C01B 7/0706* (2013.01);
(Continued)

(58) Field of Classification Search
CPC .... C07C 17/389; B01D 53/68; B01D 53/685; B01D 53/70; B01D 2253/106;
(Continued)

(56) References Cited

U.S. PATENT DOCUMENTS 3,387,430 A    6/1968  Sarvadi
2017/0158586 A1*  6/2017  Collier ............... B01D 53/8662

FOREIGN PATENT DOCUMENTS

EP    0939071 B1    1/1999
FR    1129260       1/1957
(Continued)

OTHER PUBLICATIONS

Elsheikh et al, FR 2690686 (machine translation), Nov. 1993.*

*Primary Examiner* — Jafar F Parsa
(74) *Attorney, Agent, or Firm* — Joanne Rossi

(57) ABSTRACT

Disclosed is a process for treating a gas stream containing hydrochloric acid, hydrofluoric acid, a fluorinated compound and halogenated organic compounds, wherein the gas stream is subjected to: (a) a step of washing with an acid solution to obtain a washed gas stream; (b) a step of adiabatic absorption in an aqueous solution of the hydrochloric acid contained in said washed gas stream, to collect a solution of hydrochloric acid; (c) a step of adsorption on activated carbon of the impurities present in said hydrochloric acid solution, to obtain a purified hydrochloric acid solution and a gas stream containing said fluorinated compound; and (d) a step of bringing said purified hydrochloric acid solution into contact with a silica gel. Also disclosed is a plant for the implementation of this process, and also a process for preparing a fluorinated compound comprising the catalytic pyrolysis of an organofluorine compound.

15 Claims, 1 Drawing Sheet

(51) Int. Cl.
*C01B 7/07* (2006.01)
*C07C 17/389* (2006.01)

(52) U.S. Cl.
CPC .......... *C01B 7/0725* (2013.01); *C07C 17/389* (2013.01); *B01D 2253/102* (2013.01); *B01D 2253/106* (2013.01); *B01D 2257/2045* (2013.01); *B01D 2257/2047* (2013.01); *Y02C 20/30* (2013.01)

(58) Field of Classification Search
CPC .... B01D 2257/2045; B01D 2257/2047; B01D 2253/102; C01B 7/0706; C01B 7/0725
See application file for complete search history.

(56) References Cited

FOREIGN PATENT DOCUMENTS

| | | | |
|---|---|---|---|
| GB | 1156560 | 7/1969 | |
| WO | WO 2007/079137 A2 | 7/2007 | |
| WO | WO 2008/040969 A2 | 4/2008 | |
| WO | WO 2008/054781 A1 | 5/2008 | |
| WO | WO-2015079137 A1 * | 6/2015 | ........... C07C 17/206 |

* cited by examiner

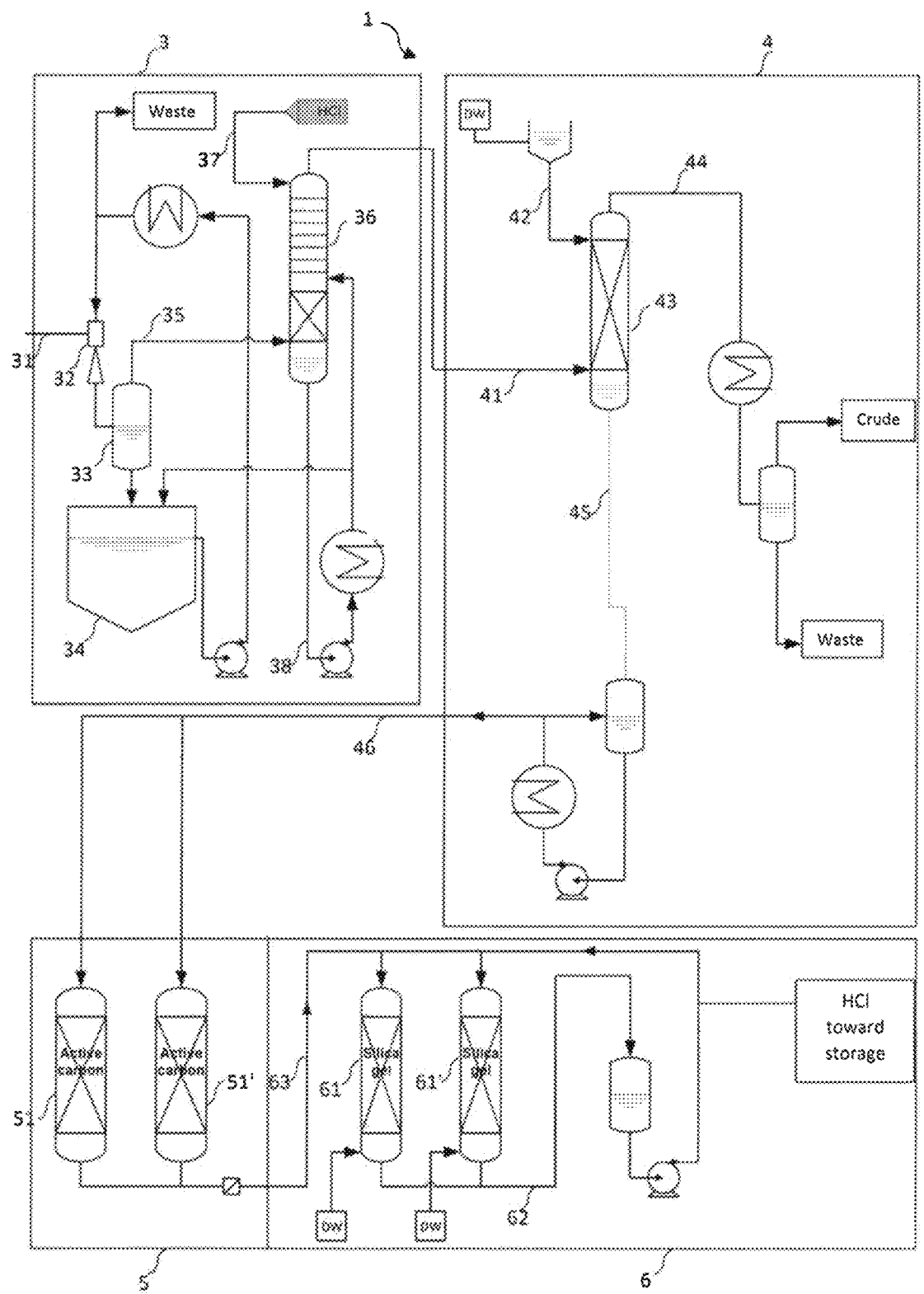

HYDROCHLORIC ACID PURIFICATION PROCESS AND PLANT

CROSS-REFERENCE TO RELATED APPLICATIONS

This application is a national stage application under 35 U.S.C. § 371 of PCT/FR2017/050864, filed Apr. 11, 2017, which claims priority based on French patent application FR.16.54010, filed May 3, 2016, the contents of each are incorporated herein by reference in their entireties.

OBJECT OF THE INVENTION

The present invention relates to a process for the purification of hydrochloric acid and to a plant suited to the implementation of this process. The invention can in particular be used in the context of the treatment of the byproducts or effluents resulting from the synthesis of a fluorinated compound from an organohalogen compound.

BACKGROUND OF THE INVENTION

It is known to produce fluorinated compounds, such as hydrofluorocarbons, by fluorination of chlorinated compounds, such as hydrochlorocarbons. This fluorination is generally a catalytic fluorination using hydrofluoric acid (HF) as fluorinating agent. During this type of reaction, hydrochloric acid (HCl) is coproduced. In practice, it is furthermore not always possible or desirable to react all of the HF involved. The latter is then re-encountered in the form of an impurity associated with the hydrochloric acid. Other reactions for the synthesis of fluorinated compounds also result in the coproduction of HCl contaminated by a small amount of HF. Such is in particular the case of the manufacture of vinylidene fluoride by pyrolysis of 1-chloro-1,1-difluoroethane.

Insofar as hydrochloric acid cannot be discharged to the environment, techniques have been provided to recover it in value. It is thus known to separate the HCl from the other gases produced (including the fluorinated compounds of interest) by adiabatic absorption in order to generate an HCl solution of commercial type and to recover, at the top, the crude gases to be treated. However, in the case where hydrochloric acid is coproduced in a pyrolysis process, it has been observed that the pyrolysis could result in the formation of tars liable to foul the adiabatic column. In addition, the HCl solution thus obtained is contaminated not only by small amounts of hydrofluoric acid (HF) but also by organic pyrolysis residues and organo-halogen compounds which constitute byproducts of the pyrolysis. This HCl solution is thus not sufficiently pure for the majority of applications.

Processes have been provided for improving the purity of an HCl solution contaminated by HF and optionally halogenated organic compounds.

Thus, the document FR 1 507 252 describes a process targeted at separating hydrofluoric acid mixed with HCl, which consists in passing this gaseous mixture into a continuous countercurrentwise washing device comprising a plate column, the washing being carried out using a concentrated aqueous hydrochloric acid solution at low temperature which is capable of absorbing the hydrofluoric acid. There are obtained, at the outlet of this column, an aqueous solution of hydrochloric acid and hydrofluoric acid, and also gaseous hydrochloric acid, depleted in HF with respect to the starting hydrochloric acid. However, in order to obtain hydrochloric acid virtually devoid of HF, it is necessary to pass the crude gas mixture over active carbon in the presence of water, upstream of the acid washing stage. It is understood that this process is thus not applicable to a crude gas mixture including a fluorinated gas of interest, which would then be trapped in the active carbon.

Furthermore, it has been suggested, in the document WO 2015/079137, that the hydrochloric acid coproduced in a catalytic fluorination process could be purified following a process involving a stage of catalytic hydrolysis of the fluorinated/oxygenated compounds present in the crude gas stream, followed by a stage of washing with an acid solution, then by a stage of adsorption of the gases on an active carbon bed and, finally, by a stage of adiabatic adsorption, making it possible to obtain an aqueous hydrochloric acid solution. This solution can optionally be subsequently purified over silica gel. This process necessarily incorporates a preliminary stage of distillation of the crude gases in order to prevent the fluorinated product of interest from being trapped in the active carbon bed employed in the catalytic hydrolysis stage. It would thus be desirable to have available a process which is not more complex than that described in the application WO 2015/079137 but which makes it possible to directly treat the crude gas stream resulting from the catalytic reaction, without it being necessary to subject it to a prior distillation.

SUMMARY OF THE INVENTION

There thus remains the need to provide an improved process for the purification of hydrochloric acid present in a crude gas stream, as a mixture with hydrofluoric acid, a fluorinated compound of interest and halogenated organic compounds, which process makes it possible to reduce both the content of hydrofluoric acid and of organic compounds and advantageously to achieve a high final concentration of hydrochloric acid.

The inventors have demonstrated that this need could be met by selecting a sequence of specific treatment stages, arranged in a predetermined order.

A first subject matter of the invention is thus a process for the treatment of a gas stream containing hydrochloric acid, hydrofluoric acid, a fluorinated compound of interest and halogenated organic compounds, in which the gas stream is successively subjected to:

(a) a stage of washing with an acid solution, in order to obtain a washed gas stream;

(b) a stage of adiabatic absorption in an aqueous solution of the hydrochloric acid present in said washed gas stream, making it possible to collect a hydrochloric acid solution and a gas stream including said fluorinated compound of interest;

(c) a stage of adsorption on active carbon of the organic impurities present in said hydrochloric acid solution, in order to obtain a purified hydrochloric acid solution; and (d) a stage of bringing said purified hydrochloric acid solution into contact with a silica gel.

A second subject matter of the invention relates to a process for the preparation of a fluorinated compound comprising:

- the catalytic fluorination of an organochlorine compound with hydrofluoric acid or the catalytic or noncatalytic pyrolysis of an organofluorine compound comprising at least one chlorine atom;
- the collection of a crude gas stream containing hydrochloric acid, hydrofluoric acid, said fluorinated compound of interest and halogenated organic compounds; and the treatment of said crude gas stream according to the process described above.

A third subject matter of the invention is a plant for the treatment of a crude gas stream containing hydrochloric acid, hydrofluoric acid, a fluorinated compound of interest and halogenated organic compounds, comprising:
- a washing unit comprising a washing column fed, on the one hand, by a pipe for conveying said crude gas stream and, on the other hand, by a pipe for conveying acid solution;
- an adiabatic absorption unit comprising a column fed, on the one hand, by a pipe for collecting washed stream resulting from the washing unit and, on the other hand, by a pipe for conveying aqueous solution;
- a pipe for collecting the fluorinated compound of interest in the gaseous form, at the outlet of the column of the adiabatic adsorption unit;
- a unit for adsorption of organic impurities, comprising an active carbon bed fed by a pipe for collecting hydrochloric acid solution resulting from the adiabatic adsorption unit;
- an additional adsorption unit connected to a pipe for collecting purified solution resulting from the unit for adsorption of impurities, and comprising a column including a silica gel.

In a preferred embodiment of the invention, the plant additionally comprises, within the washing unit, a unit for separation of heavy compounds, which is positioned upstream of the washing column, said unit for separation of heavy compounds being fed by a pipe for conveying the crude stream and connected to the washing column by a pipe for collecting detarred gas stream.

The process and the plant according to the invention make it possible to produce, on conclusion of stage (d), an aqueous hydrochloric acid solution including at least 30% by weight of hydrochloric acid, less than 10 ppm, indeed even less than 5 ppm, better still less than 1 ppm, of hydrofluoric acid and less than 150 ppm, indeed even less than 100 ppm, better still less than 50 ppm, of halogenated organic compounds.

FIGURES

FIG. 1 diagrammatically represents an embodiment of a plant according to the invention.

DETAILED DESCRIPTION

The invention is now described in greater detail and in a nonlimiting manner in the description which follows.

The invention applies in particular to the treatment of a gas stream resulting from a reaction for the synthesis of a fluorinated compound, in particular by catalytic or noncatalytic pyrolysis of an organofluorine compound comprising at least one chlorine atom or by catalytic fluorination of an organochlorine compound with hydrofluoric acid, preferably by catalytic pyrolysis of an organofluorine compound comprising at least one chlorine atom. The fluorinated compound resulting from these reactions is denoted in this description by "fluorinated compound of interest". It differs from the chlorinated and/or fluorinated compounds obtained as coproducts on conclusion of these reactions, and also from the reactants used. This fluorinated compound of interest can in particular be vinylidene fluoride (VF2).

Organochlorine compound is understood to mean an organic compound comprising one or more chlorine atoms and organofluorine compound is understood to mean an organic compound comprising one or more fluorine atoms.

It is understood that the organochlorine compound can comprise one or more fluorine atoms, just as the organofluorine compound includes at least one chlorine atom.

The organochlorine compound can be an alkane or an alkene having at least one Cl substituent and optionally at least one substituent chosen from F, I and Br (preferably F). The organofluorine compound can be an alkane or an alkene having at least one F and Cl substituent and optionally at least one substituent chosen from I and Br. The organochlorine compound and the organofluorine compound can be linear or branched, preferably linear.

The invention can be applied in particular in the following fluorination reactions:
- fluorination of perchloroethylene (PER) to give pentafluoroethane (HFC-125);
- fluorination of 1,1,1,2,3-pentachloropropane (HCC-240db) to give 2-chloro-3,3,3-trifluoropropene (HCFO-1233xf);
- fluorination of 1,1,1,2,3-pentachloropropane (HCC-240db) to give 2,3,3,3-tetrafluoropropene (HFO-1234yf);
- fluorination of 1,1,1,3,3-pentachloropropane (HCC-240fa) to give 1,3,3,3-tetrafluoropropene (HFO-1234ze);
- fluorination of 1,1,1,3,3-pentachloropropane (HCC-240fa) to give 1-chloro-3,3,3-trifluoropropene (HCFO-1233zd);
- fluorination of 2-chloro-3,3,3-trifluoropropene (HCFO-1233xf) to give 2,3,3,3-tetrafluoropropene (HFO-1234yf);
- fluorination of 1,1,2,2,3-pentachloropropane (HCC-240aa) to give 2,3,3,3-tetrafluoropropene (HFO-1234yf);
- fluorination of 1,1,2,2,3-pentachloropropane (HCC-240aa) to give 2-chloro-3,3,3-trifluoropropene (HCFO-1233xf);
- fluorination of 2,3-dichloro-1,1,1-trifluoropropane (HCFC-243db) to give 2,3,3,3-tetrafluoropropene (HFO-1234yf);
- fluorination of 2,3-dichloro-1,1,1-trifluoropropane (HCFC-243db) to give 1-chloro-3,3,3-trifluoropropene (HCFO-1233zd);
- fluorination of 2,3-dichloro-1,1,1-trifluoropropane (HCFC-243db) to give 1,3,3,3-tetrafluoropropene (HFO-1234ze);
- fluorination of 2,3-dichloro-1,1,1-trifluoropropane (HCFC-243db) to give 2-chloro-3,3,3-trifluoropropene (HCFO-1233xf);
- fluorination of 1,1,2,3-tetrachloropropene (HCO-1230xa) to give 2,3,3,3-tetrafluoropropene (HFO-1234yf);
- fluorination of 1,1,2,3-tetrachloropropene (HCO-1230xa) to give 2-chloro-3,3,3-trifluoropropene (HCFO-1233xf);
- fluorination of 2,3,3,3-tetrachloropropene (HCO-1230xf) to give 2,3,3,3-tetrafluoropropene (HFO-1234yf);
- fluorination of 2,3,3,3-tetrachloropropene (HCO-1230xf) to give 2-chloro-3,3,3-trifluoropropene (HCFO-1233xf);
- fluorination of 1,1,3,3-tetrachloropropene (HCO-1230za) to give 1-chloro-3,3,3-trifluoropropene (HCFO-1233zd);
- fluorination of 1,1,3,3-tetrachloropropene (HCO-1230za) to give 1,3,3,3-tetrafluoropropene (HFO-1234ze);
- fluorination of 1,3,3,3-tetrachloropropene (HCO-1230zd) to give 1-chloro-3,3,3-trifluoropropene (HCFO-1233zd);

fluorination of 1,3,3,3-tetrachloropropene (HCO-1230zd) to give 1,3,3,3-tetrafluoropropene (HFO-1234ze);

fluorination of 1-chloro-3,3,3-trifluoropropene (HCFO-1233zd) to give 1,3,3,3-tetrafluoropropene (HFO-1234ze);

fluorination of 1,1,2-trichloroethane to give 1-chloro-2,2-difluoroethane (HCFC-142);

fluorination of 1,2-dichloroethylene to give 1-chloro-2,2-difluoroethane (HCFC-142).

The conversion of the organochlorine compound into fluorinated compound of interest can be a direct conversion (with just one reaction stage or with just one set of reaction conditions) or an indirect conversion (with two or more than two reaction stages or by using two or more than two sets of reaction conditions). The conversion can be total or partial.

In order to avoid a rapid deactivation of the catalyst during the reaction, an oxidizing agent (for example oxygen or chlorine) can be added. It is possible, for example, to use a stream of pure oxygen or of pure chlorine, or an oxygen/nitrogen or chlorine/nitrogen mixture.

The catalyst used can, for example, be based on a metal comprising a transition metal oxide or a halide or an oxyhalide of such a metal. Mention may be made, for example, of $FeCl_3$, chromium oxyfluoride, chromium oxides (optionally subjected to fluorination treatments), chromium fluorides and their mixtures. Other possible catalysts are catalysts supported on carbon, antimony-based catalysts or aluminum-based catalysts (for example $AlF_3$ and $Al_2O_3$, aluminum oxyfluoride and aluminum fluoride). Use may be made in general of a chromium oxyfluoride, an aluminum fluoride or oxyfluoride, or a supported or nonsupported catalyst containing a metal such as Cr, Ni, Fe, Zn, Ti, V, Zr, Mo, Ge, Sn, Pb, Mg or Sb. Reference may be made in this respect to the document WO 2007/079431 (on p. 7, l. 1-5 and 28-32), to the document EP 0 939 071, to the document WO 2008/054781 (on p. 9, l. 22-p. 10, l. 34) and to the document WO 2008/040969 (Claim 1), to which documents reference is expressly made. Before its use, the catalyst is preferably subjected to an activation with air, oxygen or chlorine and/or with HF. In an alternative form, chlorine can be used as catalyst.

In a preferred embodiment, the process according to the invention is applied to a gas stream resulting from the catalytic pyrolysis of an organofluorine compound comprising at least one chlorine atom, more particularly a gas stream resulting from the pyrolytic dehydrochlorination of 1-chloro-1,1-difluoroethane to give vinylidene fluoride, according to the following reaction:

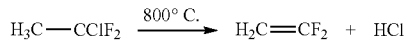

the reaction preferably being carried out in the presence of chlorine as catalyst.

The gas stream treated according to the process of the invention, which is employed in stage (a), can be directly the crude gas stream resulting from the reaction for the synthesis of the fluorinated compound of interest (such as vinylidene fluoride) or more preferably a gas stream resulting from the separation of the heavy compounds present in this crude gas stream. This separation stage is targeted at separating the gas stream to be treated according to the invention from a heavy organic fraction containing in particular tars formed during the reaction. It is preferable, according to the invention, for the gas stream to be treated, resulting from the catalytic pyrolysis or catalytic fluorination reaction or, if appropriate, from the stage of separation of heavy compounds, not be subjected beforehand to a distillation stage.

The gas stream to be treated according to the process of the invention includes hydrochloric acid, hydrofluoric acid, the fluorinated compound of interest and halogenated organic compounds, in particular organochlorine and/or organofluorine compounds. These organic compounds generally comprise the organochlorine or organofluorine reactant which has not reacted during the catalytic pyrolysis or fluorination reaction, and also the byproducts of these reactions. This gas stream generally comprises less than 30% by weight, for example less than 25% by weight, indeed even less than 20% by weight, of hydrochloric acid. In particular, when it results from the catalytic pyrolysis reaction illustrated above, the gas stream to be treated according to the invention contains, for example, vinylidene fluoride, hydrochloric acid, hydrofluoric acid and halogenated organic compounds, such as organochlorine and organofluorine compounds.

In the first stage of the process according to the invention, this gas stream is subjected to washing using an acid solution, which makes it possible to reduce the amount of hydrofluoric acid included in it. It will be possible to use, for this purpose, the acid washing process described in the application FR 1 507 252, which is incorporated here by reference, and also the acid washing plant described below.

According to one embodiment, the acid solution used during the washing stage is a solution of hydrochloric acid at a molar concentration which can range, for example, from 5% to 60%, in particular from 10% to 50%, more preferably from 20% to 45% and especially from 30% to 35%. The washing by the acid solution is preferably carried out at a temperature of 5 to 50° C. and more particularly from 7 to 40° C. and/or at a pressure of 0.1 to 4 bar, preferably of 0.3 to 2 bar, more preferably of 0.5 to 1.5 bar.

This solution preferably moves countercurrentwise with respect to the gas stream to be treated and thus becomes charged with hydrofluoric acid. A gas stream comprising hydrochloric acid and depleted in HF is then recovered on conclusion of this acid washing stage. This gas stream includes, for example, less than 500 ppm, indeed even less than 100 ppm, preferably at most 50 ppm, of HF.

In the second "adiabatic adsorption" stage of the process according to the invention, the hydrochloric acid gas stream is absorbed in demineralized water or an aqueous acid solution, in order to form an aqueous hydrochloric acid solution, while the fluorinated compound of interest is collected in the gaseous form. As the reaction for absorption of HCl in water is exothermic, it is preferable to limit the pressure at which this operation is carried out. In general, the pressure is less than 2 bar and preferably less than 1.5 bar. In this way, the absorption temperature does not exceed 130° C., and preferably 90° C. The concentration by weight of HCl in the solution resulting from the adiabatic adsorption stage can be from 5% to 50%, preferably from 15% to 40% and more particularly from 30% to 35%, and the concentration of HF can, for example, be less than 200 ppm, preferably at most 100 ppm, indeed even at most 50 ppm.

The hydrochloric acid solution resulting from the adiabatic adsorption stage is subsequently subjected to a stage of adsorption of impurities on an active carbon bed. This stage can be carried out within pressure and temperature ranges which have already been indicated above in connection with the stage of washing with an acid solution. It is preferable for the active carbon bed to be washed beforehand with hydrochloric acid in order to limit the release into the solution of ash or of inorganic or metal contaminants. This stage makes it possible to reduce the content of total organic compounds by approximately 40% to 70%, for example by 50% to 60%, and the content of volatile organic compounds by 60% to 80%, for example by approximately 70%. The impurities adsorbed by the active carbon bed are in the first place volatile organic compounds (VOCs).

On conclusion of the stage of adsorption of impurities, the temperature of the HCl solution has to be as low as possible, and for example less than or equal to 35° C., because the following stage of adsorption on silica gel is exothermic. Above this temperature, the adsorption effectiveness greatly decreases. The contact time of the purified solution of hydrochloric acid with the silica gel is between a few minutes and a few hours (for example between 10 and 60 min). The rates of passage are slow and between 1 and 20 m/h and preferably between 3 and 10 m/h. The operating pressure is a few bar (from 1 to 7 bar and preferably from 1 to 5 bar). Examples of silica gels which can be used in this invention are those sold under the reference Siogel® by Caldic and under the reference Fuji® B by Fuji Sylisia Chemical Ltd.

The fluorides content of the HCl solution at the inlet is preferably less than or equal to 100 ppm in order to avoid any risk of damage to the silica gel. In order to do this, a portion at least of the solution treated in the additional adsorption stage, thus resulting from stage (d), can be recycled in this stage, which makes it possible to increase the hydrochloric acid concentration of the solution to be treated by the silica gel and to thus reduce the HF concentration in this solution, when the concentration is initially greater than 100 ppm. After this additional stage of adsorption on silica gel, it is possible to achieve HF contents of less than 1 ppm in the HCl solution.

In an advantageous embodiment, the process according to the invention comprises a preliminary stage of separation of the heavy compounds, which makes it possible to condense the tars. This stage generally consists in bringing the crude gas stream into contact with a concentrated acid solution, under pressure, and in then releasing the gas from the liquid in order to recover a detarred gas stream.

With reference now to FIG. 1, the plant 1 according to the invention comprises four successive treatment units, namely a washing unit 3, an adiabatic absorption unit 4, a unit for adsorption of impurities 5 and an additional adsorption unit 6.

In the embodiment illustrated in FIG. 1, the stream of reaction products is first conveyed to a unit for separation of heavy compounds fed via a collecting pipe 31 at the outlet of the catalytic reactor. This unit is targeted at separating the stream of reaction products into a gas stream to be treated and into a heavy fraction containing tars. This separation unit is optional. It comprises an ejector/washer 32 fed, on the one hand, with the stream of reaction products and, on the other hand, with a concentrated acid solution. The ejector/washer brings the two fluids into contact and makes it possible both to raise the pressure level of the gas by using the acid solution as pump fluid and to lower the temperature of the gas. The mixture of fluids is subsequently transferred to a flash drum 33, which makes it possible to release the gas with respect to the liquid. The liquid fraction is sent to a decanter 34 which makes it possible to separate the heavy products. The supernatant acid solution is recovered by a pump and cooled in an exchanger before being reinjected into the ejector/washer. Purging of the HF-rich acid solution is provided at the outlet of the exchanger. The gas stream resulting from the flash drum is for its part conveyed by a feed pipe 35 into a washing column 36. The washing column 36 can be a plate column, such as a perforated plate column or a bubble cap column or a valve tray column or a column of Dualflow® type. It is preferable to use a bubble cap column. In order to limit fouling phenomena, it is also possible to use a height of random packing at the column bottom. The gas stream is preferably washed countercurrentwise: the gas stream is fed at the bottom and an acid solution is fed at the top, via a pipe for conveying acid solution 37. At the stage of washing with the acid solution, the great majority of HF of the gas stream passes into solution and is thus removed via a pipe for collecting spent acid solution 38 at the column bottom. This acid solution is cooled in a heat exchanger before being, in part, reintroduced into the washing column 36 and, in part, reinjected into the decanter 34 in order to compensate for the removal of the acid solution at the outlet of the decanter.

The washed gas stream resulting from the washing unit 3 is conveyed, via a feed pipe 41, into the adiabatic adsorption unit 4. The absorption unit 4 makes it possible to absorb the HCl from the gas stream in an aqueous solution, contributed by a pipe for introducing aqueous solution 42. This aqueous solution can be simply demineralized water or alternatively it can be an acid solution. Generally, the absorption unit 4 comprises a column 43 for bringing into contact countercurrentwise, the aqueous solution being provided at the top and the gas stream at the bottom. In order to withstand corrosion, the column 43 can be made of graphite or else of steel coated with polytetrafluoroethylene (PTFE). The column internal parts can, for example, be either made of graphite or of polyvinylidene fluoride (PVDF). A deacidified gas stream is gathered at the top, via a pipe for collecting deacidified gas stream 44. This gas stream includes the fluorinated compound of interest, for example vinylidene fluoride.

An HCl solution is gathered at the bottom, via a pipe for collecting hydrochloric acid solution 45. After cooling, this solution is conveyed, via a conveying pipe 46, toward a unit for adsorption of impurities 5, which comprises one or more columns, in this instance two columns 51 and 51', each including an active carbon bed.

After passing through one and/or other of these columns, the purified hydrochloric acid solution is subsequently sent, via a collecting pipe 63, toward an additional adsorption unit 6, which can comprise one or more columns, in this instance two columns 61 and 61', each including a silica gel. This is because it can be advantageous to have available at least two columns 51, 51' and 61, 61', so as to be able to change column once the first is saturated, without interrupting the hydrochloric acid purification process. The plant 1 additionally comprises a pipe 62 for collecting purified hydrochloric acid solution resulting from the additional adsorption unit 6.

Economic use can be made commercially of the purified HCl solution recovered on conclusion of the process of the invention.

EXAMPLES

In these examples, the concentration of fluoride ions (and thus of HF) is measured by ionometry, according to the standard additions method, using a fluorine electrode.

The total organic compounds (TOCs) are deduced from the difference between the total carbon and the inorganic carbon, measured according to the standard NF-EN-1484.

The volatile organic compounds (VOCs) are measured in two stages:

a stage of identification by gas chromatography, coupled to an electron ionization mass detector, a stage of quantification by gas chromatography.

The plant illustrated in FIG. 1 is installed as a bypass on an industrial factory for the production of vinylidene fluoride by catalytic pyrolysis of 1-chloro-1,1-difluoroethane. The crude gas stream resulting from the catalytic reactor consists of: 33% by weight of vinylidene fluoride (VF2), 19% by weight of HCl, 47% of 1-chloro-1,1-difluoroethane and 600 ppm of HF.

This crude gas stream is sent into the ejector/washer 32 of the unit for separation of heavy compounds, at a flow rate of 5120 kg/h. The temperature in the ejector/washer is 70° C. and the pressure is adjusted to 2.4 bar. The gas stream resulting from this separation unit is freed from the heavy compounds liable to form tars. It is sent to the bottom of a plate column 36, at a flow rate of 5120 kg/h. The column has a height of 1.20 meters and a diameter of five centimeters. It comprises twenty perforated plates (200 perforations per plate, each with a diameter of 1.75 mm). The distance between the plates is equal to the diameter of the column. Each plate comprises a weir which makes possible the movement of the liquid toward the column bottom, while the perforations allow the passage of the gas toward the column top. The preferred material for the column is PVDF. The column is fed with a commercial 33% by weight liquid hydrochloric acid solution, including less than 5 ppm of HF. This solution is introduced into the column 36 at a flow rate of 285 kg/h, at a temperature of 35° C. and under a pressure of 1.4 bar. The temperature of the column is 30° C. and the pressure is maintained at 1.7 bar. The liquid at the column bottom includes 59% by weight of water, 40% by weight of HCl and 0.85% by weight of HF. Its temperature is lowered to 30° C. before re-injecting it, in part, into the column and sending the other part toward the decanter 34. The gas exiting at the top of the washing column 36 at a flow rate of 5080 kg/h comprises 33.3% by weight of VF2, 47.3% by weight of 1-chloro-1,1-difluoroethane, 18.5% of HCl and 100 ppm of HF.

The gas stream resulting from the column 36 is subsequently treated on the adiabatic column 43, which is fed with demineralized water, making possible the absorption of the hydrochloric acid. The gas exiting at the adiabatic column top essentially includes VF2 and $CClF_2$—$CH_3$ (50/50 as molar %) and contains only traces of HCl. A concentrated 33% HCl solution is obtained at the adiabatic column bottom, which solution contains organohalogen compounds resulting from the pyrolysis, predominantly $C_2$ chlorine compounds, such as $Cl_2C$=$CCl_2$ (F1110), $CHCl_2$—$CHCl_2$ (F130), $CH_2Cl$—$CCl_3$ (F130A), $CH_2Cl$—$CHF_2$ (F142), and also residual $CClF_2$—$CH_3$ (F142B). This solution includes 200 ppm of total organic compounds (TOCs) and 100 ppm of volatile organic compounds (VOCs).

These organic compounds are subsequently separated by passing this aqueous solution over the active carbon bed 51 of the unit for adsorption of impurities 5, at a flow rate of 2850 kg/h. The temperature of the bed is 35° C. and the pressure is 0.4 bar. This stage makes it possible to reduce the contents of TOCs and VOCs to 100 ppm and 30 ppm respectively.

The aqueous solution exiting from the unit 5 is directed toward the additional adsorption unit 6, into the column 61, at a flow rate of 7600 kg/h. The column 61 comprises a silica gel bed maintained at a temperature of 35° C., which becomes saturated with HF on contact with the solution. The aqueous HCl solution recovered at the column bottom is, in part, directed toward a storage tank, the other part being recycled at the top of the column 61 and mixed with the aqueous solution originating from the unit for adsorption of impurities. It is thus possible to reduce the HF concentration from 200 ppm to 75 ppm at the column inlet and to promote the additional treatment over silica gel. The recycling flow rate is, in this example, 4750 kg/h. An aqueous hydrochloric acid solution including an undetectable amount of HF is thus obtained. The bed is subsequently regenerated by washing with water. A solution containing dilute hydrofluoric acid is thus generated, which has to be destroyed.

The invention claimed is:

1. A process for the treatment of a gas stream containing hydrochloric acid, hydrofluoric acid, a fluorinated compound of interest and halogenated organic compounds, in which the gas stream is successively subjected to:
    (a) a stage of washing with an acid solution in order to obtain a washed gas stream;
    (b) a stage of adiabatic absorption in an aqueous solution of the hydrochloric acid present in said washed gas stream, in order to collect a hydrochloric acid solution and a gas stream including said fluorinated compound of interest;
    (c) a stage of adsorption on active carbon of the organic impurities present in said hydrochloric acid solution, in order to obtain a purified hydrochloric acid solution; and
    (d) a stage of bringing said purified hydrochloric acid solution into contact with a silica gel.

2. The process as claimed in claim 1, characterized in that said gas stream employed in stage (a) is a crude gas stream resulting from a reaction for the synthesis of the fluorinated compound of interest.

3. The process as claimed in claim 1, characterized in that said gas stream employed in stage (a) results from the separation of the heavy compounds present in the crude gas stream resulting from a reaction for the synthesis of a fluorinated compound of interest.

4. The process as claimed in claim 3, characterized in that the process comprises a preliminary stage of separation of the heavy compounds which consists in bringing the crude gas stream into contact with a concentrated acid solution, under pressure, and then releasing the gas from the liquid in order to recover a detarred gas stream.

5. The process of claim 2, characterized in that the synthesis of the fluorinated compound of interest is carried out by pyrolysis of an organofluorine compound comprising at least one chlorine atom or by catalytic fluorination of an organochlorine compound with hydrofluoric acid.

6. The process of claim 1, characterized in that a portion at least of the solution resulting from stage (d) is recycled in stage (d).

7. The process of claim 1, characterized in that the aqueous hydrochloric acid solution resulting from stage (d) includes at least 30% by weight of hydrochloric acid, less than 10 ppm of hydrofluoric acid and less than 150 ppm of halogenated organic compounds.

8. The process of claim 1, characterized in that the gas stream is not subjected beforehand to a distillation stage.

9. A process for the preparation of a fluorinated compound of interest, comprising:
    the catalytic or noncatalytic pyrolysis of an organofluorine compound comprising at least one chlorine atom or the catalytic fluorination of an organochlorine compound with hydrofluoric acid;

the collection of a crude gas stream containing hydrochloric acid, hydrofluoric acid, said fluorinated compound of interest and halogenated organic compounds; and the treatment of said crude gas stream according to the process as claimed in claim 1.

10. The process of claim 1, characterized in that in stage (a) the acid solution comprises hydrochloric acid solution.

11. The process of claim 1, characterized in that the fluorinated compound of interest comprises vinylidene fluoride.

12. The process of claim 5, characterized in that the synthesis of the fluorinated compound of interest is carried out by catalytic pyrolysis.

13. The process of claim 9, characterized in that pyrolysis is catalytic.

14. The process of claim 1, characterized in that the fluorinated compounds of interested are the reaction product of a catalytic or noncatalytic pyrolysis of an organofluorine compound comprising at least one chlorine atom or a catalytic fluorination of an organochlorine compound with hydrofluoric acid, and wherein the halogenated organic compounds comprise the chlorinated and/or fluorinated compounds obtained as coproducts of said catalytic or noncatalytic pyrolysis or said catalytic fluorination, and any remaining reactants of said catalytic or noncatalytic pyrolysis or said catalytic fluorination.

15. The process of claim 1, characterized in that the fluorinated compounds of interested are selected from the group consisting of:
vinylidene fluoride;
pentafluoroethane (HFC-125);
1-chloro-2,2-difluoroethane (HCFC-142);
1,3,3,3-tetrafluoropropene (HFO-1234ze);
2,3,3,3-tetrafluoropropene (HFO-1234yf);
1-chloro-3,3,3-trifluoropropene (HCFO-1233zd);
2-chloro-3,3,3-trifluoropropene (HCFO-1233xf);
and wherein the halogenated organic compounds do not include the fluorinated compounds of interested.

* * * * *